United States Patent [19]

Nakahashi

[11] 4,300,812
[45] Nov. 17, 1981

[54] OPTICAL SYSTEM FOR ENDOSCOPES

[75] Inventor: Ken-ichi Nakahashi, Hachiouji, Japan

[73] Assignee: Olympus Optical Co., Ltd., Tokyo, Japan

[21] Appl. No.: 37,214

[22] Filed: May 8, 1979

[30] Foreign Application Priority Data

May 15, 1978 [JP] Japan .................................. 53-56518

[51] Int. Cl.³ .............................................. G02B 7/04
[52] U.S. Cl. ............................................... 350/42
[58] Field of Search ......................................... 350/42

[56] References Cited

U.S. PATENT DOCUMENTS 3,608,998  9/1971  Rinker ................................... 350/42

Primary Examiner—John K. Corbin
Assistant Examiner—Matthew W. Koren
Attorney, Agent, or Firm—Cushman, Darby & Cushman

[57] ABSTRACT

An optical system for endoscopes comprising an objective lens, a plural number of relay lenses for consecutively transferring the image formed with said objective lens and an eyepiece. In said optical system, the whole or portion of one of said relay lenses can be displaced along the optical axis to vary magnification level of said optical system.

1 Claim, 1 Drawing Figure

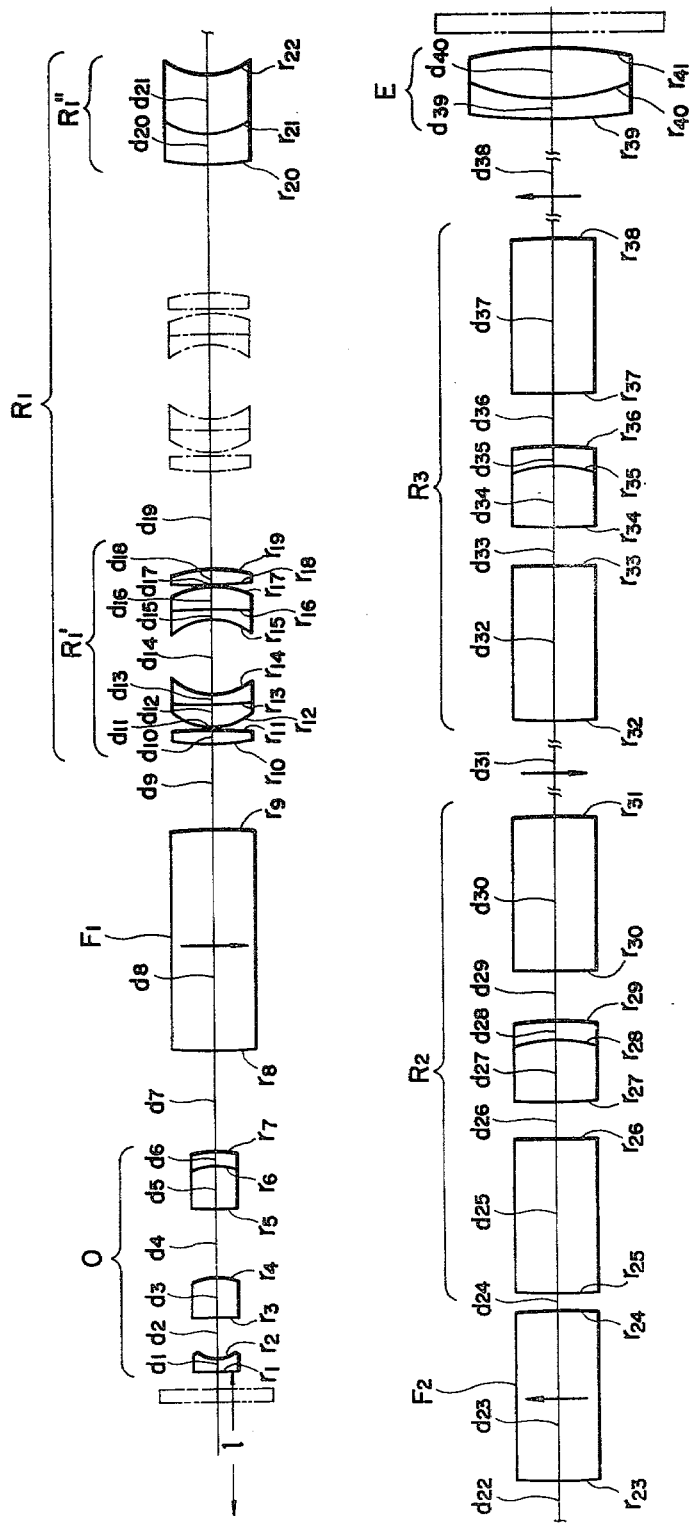

OPTICAL SYSTEM FOR ENDOSCOPES

BACKGROUND OF THE INVENTION (a) Field of the Invention

The present invention relates to an optical system for hard (or non-flexible) endoscopes and, more specifically, to an optical system in which one of plural relay lenses is designed as a variable-magnification lens system.

(b) Description of the Prior Art

In medical examinations through an endoscope, it is desired to magnify locations to be observed through the endoscope. In order to satisfy such a desire, it has conventionally been practised to displace the distal end of the endoscope from its normal position to another which is closer to the object to be observed and correct out-of-focus thereby caused by displacing the eyepiece in the optical system.

However, such a method has a defect that it does not permit observing images at a sufficiently high magnification for the following reasons: (1) it is impossible to displace the objective lens to a position sufficiently close to the object to be observed since the front focal point of the objective lens of the optical system is located inside the objective lens itself and (2) when the objective lens is displaced closer to the object to be observed, it is impossible to correct out-of-focus since movable range of the eyepiece is restricted.

As a second method to enable observation of images both at the normal size and a magnified size, it is practised to prepare objective lenses designed for different magnification levels and replace them with each other for observation. However, this method also has the following defects: (1) it is required to prepare additional objective lenses, (2) the endoscope requires tedious procedures to take it out of the body cavity for replacing the objective lens with another and the location to be observed may be lost out of sight when the endoscope is inserted once again into the body cavity and (3) the patient must suffer from much pain while the endoscope is inserted and taken out repeatedly.

A third method to observe a location at a magnified size is to use an eyepiece designed as a variable-magnification lens system in an endoscope. In such an endoscope, however, brightness is different on image at the normal size and one at magnified size since an image formed with the rays which have passed through the objective lens and relay lenses is magnified by the eyepiece. Therefore, the third method has a defect that images are darkened especially at the high magnification level required for minute observation.

In addition to the above-mentioned methods, it can be contrived to design an objective lens of an endoscope as a zoom lens system. However, a zoom lens system of the mechanical compensation type requires a complicated displacing mechanism and it is impossible to arrange a displacing mechanism in the distal end of an endoscope which must have a diameter as small as possible. Further, an objective lens system for an endoscope is very small and comprises practically no space that permits displacing specific lenses for zooming. It is therefore practically impossible to adopt a zoom lens system of optical compensation type as an objective lens system of an endoscope.

SUMMARY OF THE INVENTION

A general object of the present invention is to provide an optical system for endoscopes which permits observing images both at the normal size and a magnified size by displacing one of relay lens systems or portion thereof in an optical system of said endoscope comprising an objective lens, relay lenses and an eyepiece.

BRIEF DESCRIPTION OF THE DRAWING

The accompanying drawing shows a sectional view illustrating the composition of the optical system for endoscopes according to the present invention.

DETAILED DESCRIPTION OF PREFERRED EMBODIMENT

Referring now to the accompanying drawing, a preferred embodiment will be described in details for better understanding of the present invention. In the accompanying drawing illustrating the composition of the optical system for endoscopes, the reference symbol O represents an objective lens, the reference symbols $F_1$ and $F_2$ designate field lenses respectively, the reference symbols $R_1$ through $R_3$ denote relay lenses respectively and the reference symbol E represents an eyepiece. In the embodiment illustrated in the drawing, the relay lens $R_1$ which is arranged nearest the objective lens O among the relay lenses is designed as a variable-magnification lens system. Speaking more concretely, the relay lens $R_1$ is divided into a movable lens $R_1'$ and fixed lens $R_1''$, and the movable lens $R_1'$ can be displaced between the positions shown in solid lines and chain lines respectively to set the optical system at different magnification levels.

When the movable lens $R_1'$ is set at the position shown in the solid lines, it is focused on the image formed with the objective lens O and let us assume that the movable lens is set at a magnification level $\beta_1$ in this condition. Further, the fixed lens $R_1''$ in the relay lens $R_1$ forms an image at a magnification level $\beta_1$ at a predetermined position before the relay lens $R_2$ (in the field lens $F_2$ shown in the drawing). The image formed by this relay lens is focused consecutively by the relay lenses $R_2$, $R_3$ ... for transferring. Then, let us assume that the movable lens is displaced to the position shown in the chain lines to set it at a magnification level of $1/\beta_1$. In this condition, the image formed by the movable lens $R_1'$ remains at the same place. Hence, the fixed lens $R_1''$ forms an image at the same position as that formed when the movable lens $R_1'$ is placed at the position shown in the solid lines. When the movable lens $R_1'$ is placed at the position shown in the solid lines, the image formed by the objective lens is focused by the relay lens $R_1$ at a magnification of $\beta_1 \times \beta_2$. When the movable lens $R_1'$ is placed at the position shown in the chain lines, however, magnification level of the relay lens $R_1$ changes into $1/\beta_1 \times \beta_2$. Since $\beta_1 = 2.0$ and $\beta_2 = 2.0$ as is clarified by the numerical data hereinafter described, the relay lens is designed as a lens system changing magnification at a ratio of 1:4.

The embodiment described above uses the relay lens $R_1$ as a variable-magnification lens system in which the movable lens $R_1'$ of the relay lens $R_1$ can be displaced between the positions shown in the solid and chain lines respectively, whereby the endoscope can be set at high magnification level for observing location of interest at a high magnification level.

In this embodiment, the relay lens $R_1$ is divided into a movable lens $R_1'$ and fixed lens $R_1''$, and both the lenses form an image at a predetermined magnification level which is relayed at a magnification level of 1x by the relay lenses $R_2$, $R_3$ .... However, it is possible to omit the fixed lens. In case where the fixed lens is omitted, the image may be enlarged to a desired magnification level by the relay lenses arranged after the relay lens $R_2$, or by the movable lens alone. Further, the relay lens to be used as the variable-magnification lens system may not be arranged nearest the objective lens. In order to make rays incident effectively on the variable-magnification lens system, however, it is preferable to use the relay lens arranged nearest the objective lens as the variable-magnification lens system. When a relay lens arranged farther from the objective lens is to be used as the variable-magnification lens system, it is necessary to design the lens system arranged before the variable-magnification lens system so as to allow sufficient quantity of rays to be incident on the variable-magnification lens system.

In addition to the embodiment described above, it will be possible to observe images at different magnification levels through an endoscope by designing a relay lens as a zoom lens system in the endoscope. In case where the zoom lens system is of a mechanical composition type, however, it requires a mechanical elements such as a cam mechanism which unavoidably increase diameter of the endoscope to be used therewith and cannot be practically adopted for an endoscope which must always have a small diameter. It is therefore necessary to design a variable-magnification lens system of an optical compensation type.

Further, it may be contrived to arrange plural lenses on a drum which permits switching said lenses in an endoscope. However, such a drum also requires a wide space in the endoscope and is practically incompatible with an endoscope.

Now, numerical data for the embodiment described above with reference to the accompanying drawing will be clarified below:

$f = 1$

| | | | |
|---|---|---|---|
| $r_1 = \infty$ | | | |
| | $d_1 = 0.0321$ | $n_1 = 1.7880$ | $\nu_1 = 47.43$ |
| $r_2 = 0.1048$ | | | |
| | $d_2 = 0.1413$ | | |
| $r_3 = -1.8540$ | | | |
| | $d_3 = 0.1284$ | $n_2 = 1.6860$ | $\nu_2 = 49.16$ |
| $r_4 = -0.2063$ | | | |
| | $d_4 = 0.2081$ | | |
| $r_5 = 5.0094$ | | | |
| | $d_5 = 0.1359$ | $n_3 = 1.62041$ | $\nu_3 = 60.27$ |
| $r_6 = -0.1536$ | | | |
| | $d_6 = 0.0423$ | $n_4 = 1.84666$ | $\nu_4 = 23.90$ |
| $r_7 = -0.2960$ | | | |
| | $d_7 = 0.3130$ | | |
| $r_8 = 1.0901$ | | | |
| | $d_8 = 0.6993$ | $n_5 = 1.62004$ | $\nu_5 = 36.25$ |
| $r_9 = -1.0901$ | | | |
| | $d_9 = 0.99$ (variable) | | |
| $r_{10} = 0.919$ | | | |
| | $d_{10} = 0.045$ | $n_6 = 1.65830$ | $\nu_6 = 57.33$ |
| $r_{11} = 3.170$ | | | |
| | $d_{11} = 0.008$ | | |
| $r_{12} = 0.247$ | | | |
| | $d_{12} = 0.069$ | $n_7 = 1.67790$ | $\nu_7 = 55.33$ |
| $r_{13} = 1.134$ | | | |
| | $d_{13} = 0.031$ | | |
| $r_{14} = 0.204$ | | | |
| | $d_{14} = 0.235$ | | |
| $r_{15} = -0.210$ | | | |
| | $d_{15} = 0.031$ | $n_9 = 1.59551$ | $\nu_9 = 39.21$ |
| $r_{16} = -1.684$ | | | |
| | $d_{16} = 0.069$ | $n_{10} = 1.67790$ | $\nu_{10} = 55.33$ |
| $r_{17} = -0.362$ | | | |
| | $d_{17} = 0.006$ | | |
| $r_{18} = -5.860$ | | | |
| | $d_{18} = 0.044$ | $n_{11} = 1.65830$ | $\nu_{11} = 57.33$ |
| $r_{19} = -0.507$ | | | |
| | $d_{19} = 1.88$ (variable) | | |
| $r_{10} = 0.884$ | | | |
| | $d_{20} = 0.096$ | $n_{12} = 1.56883$ | $\nu_{12} = 56.14$ |
| $r_{21} = 0.224$ | | | |
| | $d_{21} = 0.192$ | $n_{13} = 1.61659$ | $\nu_{13} = 36.63$ |
| $r_{22} = 0.243$ | | | |
| | $d_{22} = 0.6046$ | | |
| $r_{23} = 1.6829$ | | | |
| | $d_{23} = 0.6426$ | $n_{14} = 1.62004$ | $\nu_{14} = 36.25$ |
| $r_{24} = -1.6829$ | | | |
| | $d_{24} = 0.0465$ | | |
| $r_{25} = 1.4110$ | | | |
| | $d_{25} = 3.3109$ | $n_{15} = 1.62004$ | $\nu_{15} = 36.25$ |
| $r_{26} = \infty$ | | | |
| | $d_{26} = 0.1182$ | | |
| $r_{27} = 1.8607$ | | | |
| | $d_{27} = 0.1980$ | $n_{16} = 1.65160$ | $\nu_{16} = 58.67$ |
| $r_{28} = -0.4708$ | | | |
| | $d_{28} = 0.0658$ | $n_{17} = 1.80610$ | $\nu_{17} = 40.95$ |
| $r_{29} = -1.0354$ | | | |
| | $d_{29} = 0.1696$ | | |
| $r_{30} = \infty$ | | | |
| | $d_{30} = 3.3109$ | $n_{18} = 1.62004$ | $\nu_{18} = 36.25$ |
| $r_{31} = -1.4110$ | | | |
| | $d_{31} = 0.5190$ | | |
| $r_{32} = 1.4110$ | | | |
| | $d_{32} = 3.3109$ | $n_{19} = 1.62004$ | $\nu_{19} = 36.25$ |
| $r_{33} = \infty$ | | | |
| | $d_{33} = 0.1182$ | | |
| $r_{34} = 1.8607$ | | | |
| | $d_{34} = 0.1980$ | $n_{20} = 1.65160$ | $\nu_{20} = 58.67$ |
| $r_{35} = -0.4708$ | | | |
| | $d_{35} = 0.0658$ | $n_{21} = 1.80610$ | $\nu_{21} = 40.95$ |
| $r_{36} = -1.0354$ | | | |
| | $d_{36} = 0.1696$ | | |
| $r_{37} = \infty$ | | | |
| | $d_{37} = 3.3109$ | $n_{22} = 1.62004$ | $\nu_{22} = 36.25$ |
| $r_{38} = -1.4110$ | | | |
| | $d_{38} = 1.4141$ | | |
| $r_{39} = 2.2095$ | | | |
| | $d_{39} = 0.0642$ | $n_{23} = 1.78472$ | $\nu_{23} = 25.7$ |
| $r_{40} = 0.6153$ | | | |
| | $d_{40} = 0.1605$ | $n_{24} = 1.67003$ | $\nu_{24} = 47.3$ |
| $r_{41} = -1.0717$ | | | |

(Note: $d_{12} = 0.069$ with $n_7 = 1.67790$, $\nu_7 = 55.33$; $d_{13} = 0.031$ with $n_8 = 1.62606$, $\nu_8 = 39.10$)

wherein the reference symbol f represents focal length of the relay lens $R_1$, the reference symbols $r_1$ through $r_{41}$ designate radii of curvature of the respective surfaces, the reference symbol $d_1$ through $d_{40}$ denote thicknesses of the respective lens elements and airspaces therebetween, the reference symbols $n_1$ through $n_{24}$ represent refractive indices of the respective lens elements and the reference symbols $\nu_1$ through $\nu_{24}$ designate Abbe's numbers of the respective lens elements.

In the numerical data clarified above, the reference symbol $d_9$ represents the airspace between the field lens $F_1$ and the relay lens $R_1$ when the movable lens $R_1'$ is set at the position shown in the solid lines. When the movable lens is placed at the position shown in the chain lines, the reference symbols $d_9$ and $d_{19}$ have values of 2.40 and 0.48 respectively.

It is possible to set the endoscope according to the present invention described above at different magnification level for observation by changing the distance as measured from its distal end to the object to be observed. By using the endoscope in this mode, it is possible to change magnification of the endoscope within a range wider than that available by displacing the movable lens and obtain the effect similar to that available with an endoscope comprising a zoom lens system. In case where the endoscope comprises the variable-magnification lens system having the above-described numerical data, magnification levels are variable as follows by changing the distance as measured from its distal end to the object to be observed:

| Distance l as measured from distal end to object to be observed | $d_9$ | $d_{19}$ | Overall magnification |
|---|---|---|---|
| 4.28 | 2.39 | 0.49 | 0.52 |
| 4.28 | 0.93 | 1.94 | 2.01 |
| 2.68 | 2.40 | 0.48 | 0.81 |
| 2.68 | 0.94 | 1.93 | 3.15 |
| 1.61 | 2.40 | 0.48 | 1.33 |
| 1.61 | 0.97 | 1.88 | 5.01 |
| 1.07 | 2.40 | 0.48 | 1.96 |
| 1.07 | 0.99 | 1.89 | 7.21 |
| 0.54 | 2.39 | 0.49 | 3.67 |
| 0.54 | 1.03 | 1.84 | 12.89 |

The objective lens and eyepiece used in the embodiment are designed for magnification levels of 0.128 (in case of design standard value for a distance of the object to be observed of 1.61) and 10.41 respectively.

As is understood from the foregoing descriptions, the endoscope according to the present invention comprises relay lenses one of which is designed as a variable-magnification lens system having such a composition as described with reference to the preferred embodiment or an optical compensation type zoom lens system, and is so adapted as to permit changing magnification level by displacing said relay lens designed as the variable-magnification lens system as a whole or portion thereof linearly along the optical axis. Therefore, the present invention makes it possible to design an endoscope having a small diameter even when it comprises a variable-magnification lens system and being easily switchable for observation of image at a sufficiently high magnification level.

I claim:

1. An optical system for endoscopes comprising an objective lens, a field lens, a variable-magnification relay lens system, another field lens, two relay lens systems, and an eyepiece arranged in the order from the object side, said optical system for endoscopes having the following numerical data:

$f = 1$ $r_1 = \infty$
$\quad d_1 = 0.0321 \quad n_1 = 1.7880 \quad \nu_1 = 47.43$
$r_2 = 0.1048$
$\quad d_2 = 0.1413$
$r_3 = -1.8540$
$\quad d_3 = 0.1284 \quad n_2 = 1.6860 \quad \nu_2 = 49.16$
$r_4 = -0.2063$
$\quad d_4 = 0.2081$
$r_5 = 5.0094$
$\quad d_5 = 0.1359 \quad n_3 = 1.62041 \quad \nu_3 = 60.27$
$r_6 = -0.1536$
$\quad d_6 = 0.0423 \quad n_4 = 1.84666 \quad \nu_4 = 23.90$
$r_7 = -0.2960$
$\quad d_7 = 0.3130$
$r_8 = 1.0901$
$\quad d_8 = 0.6993 \quad n_5 = 1.62004 \quad \nu_5 = 36.25$ -continued $r_9 = -1.0901$
$\quad d_9 = 0.99 \text{ (variable)}$
$r_{10} = 0.919$
$\quad d_{10} = 0.045 \quad n_6 = 1.65830 \quad \nu_6 = 57.33$
$r_{11} = 3.170$
$\quad d_{11} = 0.008$
$r_{12} = 0.247$
$\quad d_{12} = 0.069 \quad n_7 = 1.67790 \quad \nu_7 = 55.33$
$r_{13} = 1.134$
$\quad d_{13} = 0.031 \quad n_8 = 1.62606 \quad \nu_8 = 39.10$
$r_{14} = 0.204$
$\quad d_{14} = 0.235$
$r_{15} = -0.210$
$\quad d_{15} = 0.031 \quad n_9 = 1.59551 \quad \nu_9 = 39.21$
$r_{16} = -1.684$
$\quad d_{16} = 0.069 \quad n_{10} = 1.67790 \quad \nu_{10} = 55.33$
$r_{17} = -0.362$
$\quad d_{17} = 0.006$
$r_{18} = -5.860$
$\quad d_{18} = 0.044 \quad n_{11} = 1.65830 \quad \nu_{11} = 57.33$
$r_{19} = -0.507$
$\quad d_{19} = 1.88 \text{ (variable)}$
$r_{20} = 0.884$
$\quad d_{20} = 0.096 \quad n_{12} = 1.56883 \quad \nu_{12} = 56.14$
$r_{21} = 0.224$
$\quad d_{21} = 0.192 \quad n_{13} = 1.61659 \quad \nu_{13} = 36.63$
$r_{22} = 0.243$
$\quad d_{22} = 0.6046$
$r_{23} = 1.6829$
$\quad d_{23} = 0.6426 \quad n_{14} = 1.62004 \quad \nu_{14} = 36.25$
$r_{24} = -1.6829$
$\quad d_{24} = 0.0465$
$r_{25} = 1.4110$
$\quad d_{25} = 3.3109 \quad n_{15} = 1.62004 \quad \nu_{15} = 36.25$
$r_{26} = \infty$
$\quad d_{26} = 0.1182$
$r_{27} = 1.8607$
$\quad d_{27} = 0.1980 \quad n_{16} = 1.65160 \quad \nu_{16} = 58.67$
$r_{28} = -0.4708$
$\quad d_{28} = 0.0658 \quad n_{17} = 1.80610 \quad \nu_{17} = 40.95$
$r_{29} = -1.0354$
$\quad d_{29} = 0.1696$
$r_{30} = \infty$
$\quad d_{30} = 3.3109 \quad n_{18} = 1.62004 \quad \nu_{18} = 36.25$
$r_{31} = -1.4110$
$\quad d_{31} = 0.5190$
$r_{32} = 1.4110$
$\quad d_{32} = 3.3109 \quad n_{19} = 1.62004 \quad \nu_{19} = 36.25$
$r_{33} = \infty$
$\quad d_{33} = 0.1182$
$r_{34} = 1.8607$
$\quad d_{34} = 0.1980 \quad n_{20} = 1.65160 \quad \nu_{20} = 58.67$
$r_{35} = -0.4708$
$\quad d_{35} = 0.0658 \quad n_{21} = 1.80610 \quad \nu_{21} = 40.95$
$r_{36} = -1.0354$
$\quad d_{36} = 0.1696$
$r_{37} = \infty$
$\quad d_{37} = 3.3109 \quad n_{22} = 1.62004 \quad \nu_{22} = 36.25$
$r_{38} = -1.4110$
$\quad d_{38} = 1.4141$
$r_{39} = 2.2095$
$\quad d_{39} = 0.0642 \quad n_{23} = 1.78472 \quad \nu_{23} = 25.7$
$r_{40} = 0.6153$
$\quad d_{40} = 0.1605 \quad n_{24} = 1.67003 \quad \nu_{24} = 47.3$
$r_{41} = -1.0717$ wherein reference symbols $r_1$ through $r_{41}$ respectively represent radii of curvature of respective lens surfaces, reference symbols $d_1$ through $d_{40}$ respectively represent thicknesses or respective lenses and airspaces between respective lenses, reference symbols $n_1$ through $n_{24}$ respectively represent refractive indices of respective lenses, and reference symbols $\nu_1$ through $\nu_{24}$ respectively represent Abbe's numbers of respective lenses.

* * * * *